(12) United States Patent
Smith

(10) Patent No.: US 12,734,076 B2
(45) Date of Patent: Sep. 15, 2026

(54) FEMININE HYGIENE UNDERGARMENT

(71) Applicant: Felicia Anita Smith, Spokane, WA (US)

(72) Inventor: Felicia Anita Smith, Spokane, WA (US)

( * ) Notice: Subject to any disclaimer, the term of this patent is extended or adjusted under 35 U.S.C. 154(b) by 282 days.

(21) Appl. No.: 18/615,832

(22) Filed: Mar. 25, 2024

(65) Prior Publication Data

US 2024/0325215 A1 Oct. 3, 2024

Related U.S. Application Data

(60) Provisional application No. 63/577,046, filed on Mar. 27, 2023.

(51) Int. Cl.

*A61F 13/15* (2006.01)
*A61F 13/496* (2006.01)
*A61L 15/26* (2006.01)
*A61L 15/42* (2006.01)
*A61F 13/49* (2006.01)
*A61F 13/494* (2006.01)

(52) U.S. Cl.

CPC ............ *A61F 13/496* (2013.01); *A61L 15/26* (2013.01); *A61L 15/42* (2013.01); *A61F 2013/49022* (2013.01); *A61F 2013/4909* (2013.01); *A61F 2013/49486* (2013.01)

(58) Field of Classification Search

CPC .......... A61F 13/496; A61F 2013/49022; A61F 2013/4909; A61F 2013/49486; A61L 15/26; A61L 15/42

USPC ............. 604/385.01, 385.25, 396, 401; 2/73, 2/78.3, 109, 400, 406, 222, 223

See application file for complete search history.

(56) References Cited

U.S. PATENT DOCUMENTS

2005/0261658 A1* 11/2005 Baumchen ............ A61F 13/505 604/402
2011/0224639 A1* 9/2011 Venable ................ A61F 13/496 604/385.01
2023/0225437 A1* 7/2023 Carlino .................... A41D 1/06 2/79
2024/0325215 A1* 10/2024 Smith ..................... A61L 15/42

* cited by examiner

*Primary Examiner* — Jacqueline F Stephens
(74) *Attorney, Agent, or Firm* — Gulf Coast Intellectual Property Group

(57) ABSTRACT

A feminine hygiene product that is formed in a boxer short style wherein the present invention includes a body having a first layer and a second layer. The body of the present invention includes a front wall panel and a rear wall panel that provide substantial coverage of the pelvic area of a wearer. A pair of opposing side panels are operably coupled intermediate the front wall panel and rear wall panel. The opposing side panels are manufactured from an elastane or similar material. The second layer of the body is manufactured from a superabsorbent polymer or similar material. The body includes upper leg portions having a lower perimeter edge. Integrally formed with the lower perimeter edge of the upper leg portions are tab members. Tab member extend downward from the lower perimeter edge and are present between the front wall panel and rear wall panel adjacent the groin area.

4 Claims, 2 Drawing Sheets

60
68
44
40
42
66
65
24
20
22

FEMININE HYGIENE UNDERGARMENT

PRIORITY UNDER 35 U.S.C SECTION 119 (E) & 37 C.E.R. SECTION 1.78

This nonprovisional application claims priority based upon the following prior U.S. Provisional Patent Application No. 63/577,046 filed Mar. 27, 2023, in the name of Felicia Anita Smith, which is hereby incorporated by reference for all purposes.

FIELD OF THE INVENTION

The present invention relates generally to feminine hygiene products, more specifically but not by way of limitation, a boxer style undergarment that is operable to be worn by women during menstruation wherein the present invention is manufactured from a first and second layer and is configured to provide substantial coverage of the pelvic area of the wearer.

BACKGROUND

Sanitary napkins can be utilized by women to help with issues such as but not limited to menstruation fluid control and bladder incontinence. These products help keep fluids such as blood and urine from egressing onto clothes and the like. Conventional sanitary napkins and adult diaper style devices are commercially available in various sizes and styles. The commercially available styles perform the same basic task and choice thereof is made based on a variety of personal reasons. Styles available for menstruation typically include tampons and pads.

One issue with existing sanitary napkins is their inability to control heavy periods of menstruation. Furthermore, conventionally available styles of sanitary napkins may not work well when the wearer is in different body positions. By way of example but not limitation, when a wearer of a feminine hygiene product is in a prone position during a heavy menstruation cycle, conventional feminine hygiene products can leak which results in fluids egressing onto clothing and bedding which is undesirable. Another issue with conventional sanitary pads is their design lacks sufficient surface area to provide coverage that ensures no leakage of fluids. Conventional sanitary pads typically line the bottom portion of a women's underwear with typically a body that provides a slight curved portion forward and rearward of the bottom. This design has proven to be ineffective for women with heavy menstrual cycles.

Accordingly, there is a need for a feminine hygiene product that is designed having a boxer style undergarment style wherein the present invention provides improved coverage of the pelvic area with an absorbent layer so as to accommodate heavier menstrual cycles and ensure no leakage.

SUMMARY OF THE INVENTION

It is the object of the present invention to provide a feminine hygiene product configured to capture and retain bodily fluids wherein the present invention includes a body having a first layer and a second layer.

Another object of the present invention is to provide a feminine hygiene product operable to control heavy menstrual cycles of a women wherein the body includes a front wall panel and a rear wall panel.

A further object of the present invention is to provide a feminine hygiene product configured to capture and retain bodily fluids wherein the body of the present invention further includes opposing side panels operably coupled intermediate the front wall panel and rear wall panel.

Yet a further object of the present invention is to provide a feminine hygiene product operable to control heavy menstrual cycles of a women wherein the body is stitched so as to form upper leg portions having apertures for a wearer's leg to be journaled therethrough.

Still another object of the present invention is to provide a feminine hygiene product configured to capture and retain bodily fluids wherein the side panels are manufactured from a stretchable material.

An additional object of the present invention is to provide a feminine hygiene product operable to control heavy menstrual cycles of a women wherein the body further includes a waistband manufactured from the same material as the side panels.

Yet a further object of the present invention is to provide a feminine hygiene product configured to capture and retain bodily fluids wherein the body further includes tab members proximate the bottom perimeter of the upper leg portions.

To the accomplishment of the above and related objects the present invention may be embodied in the form illustrated in the accompanying drawings. Attention is called to the fact that the drawings are illustrative only. Variations are contemplated as being a part of the present invention, limited only by the scope of the claims.

BRIEF DESCRIPTION OF THE DRAWINGS

A more complete understanding of the present invention may be had by reference to the following Detailed Description and appended claims when taken in conjunction with the accompanying Drawings wherein:

DETAILED DESCRIPTION

Figure 1:
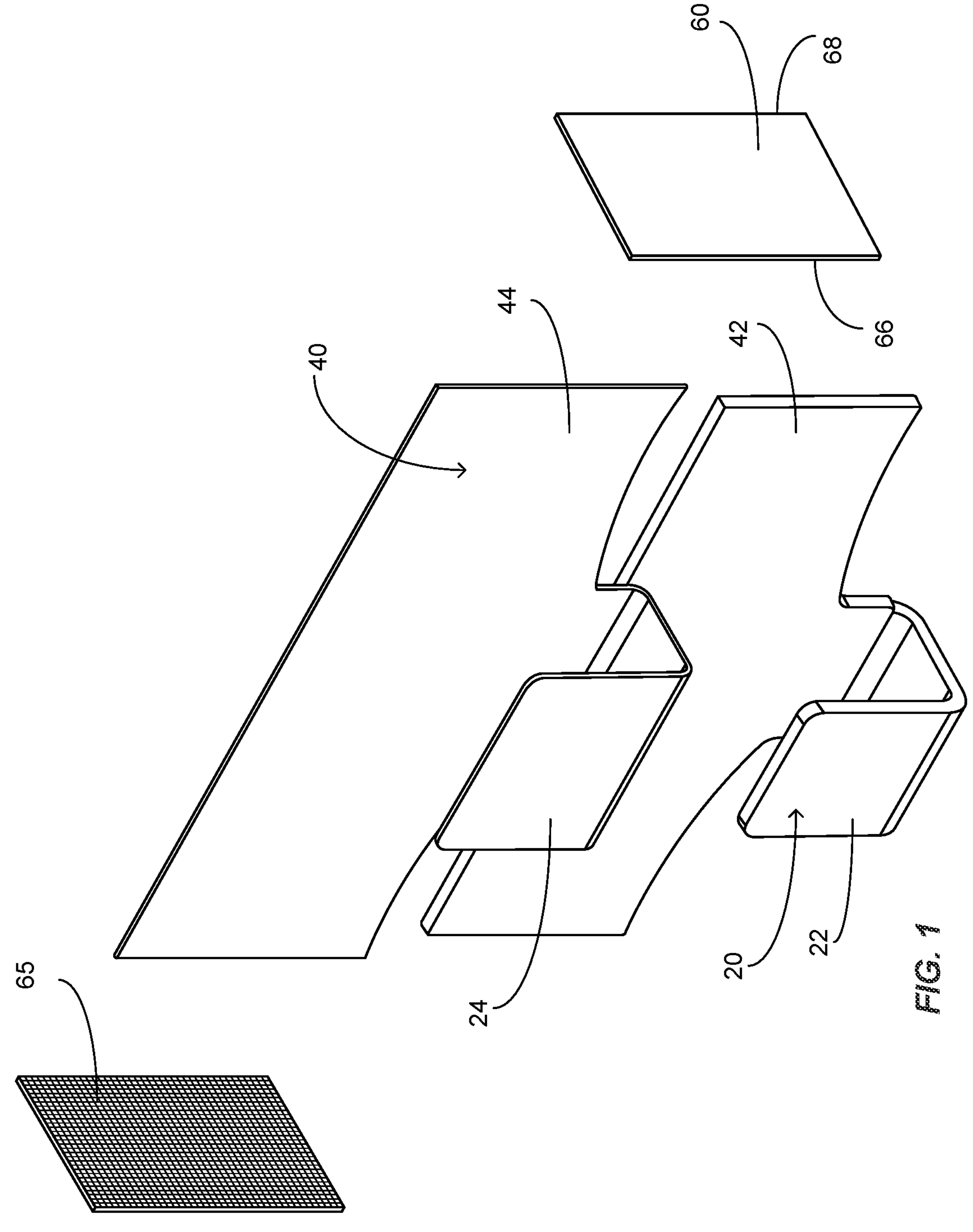
FIG. 1 is a diagrammatic view of the construction of the present invention.
Figure 2:
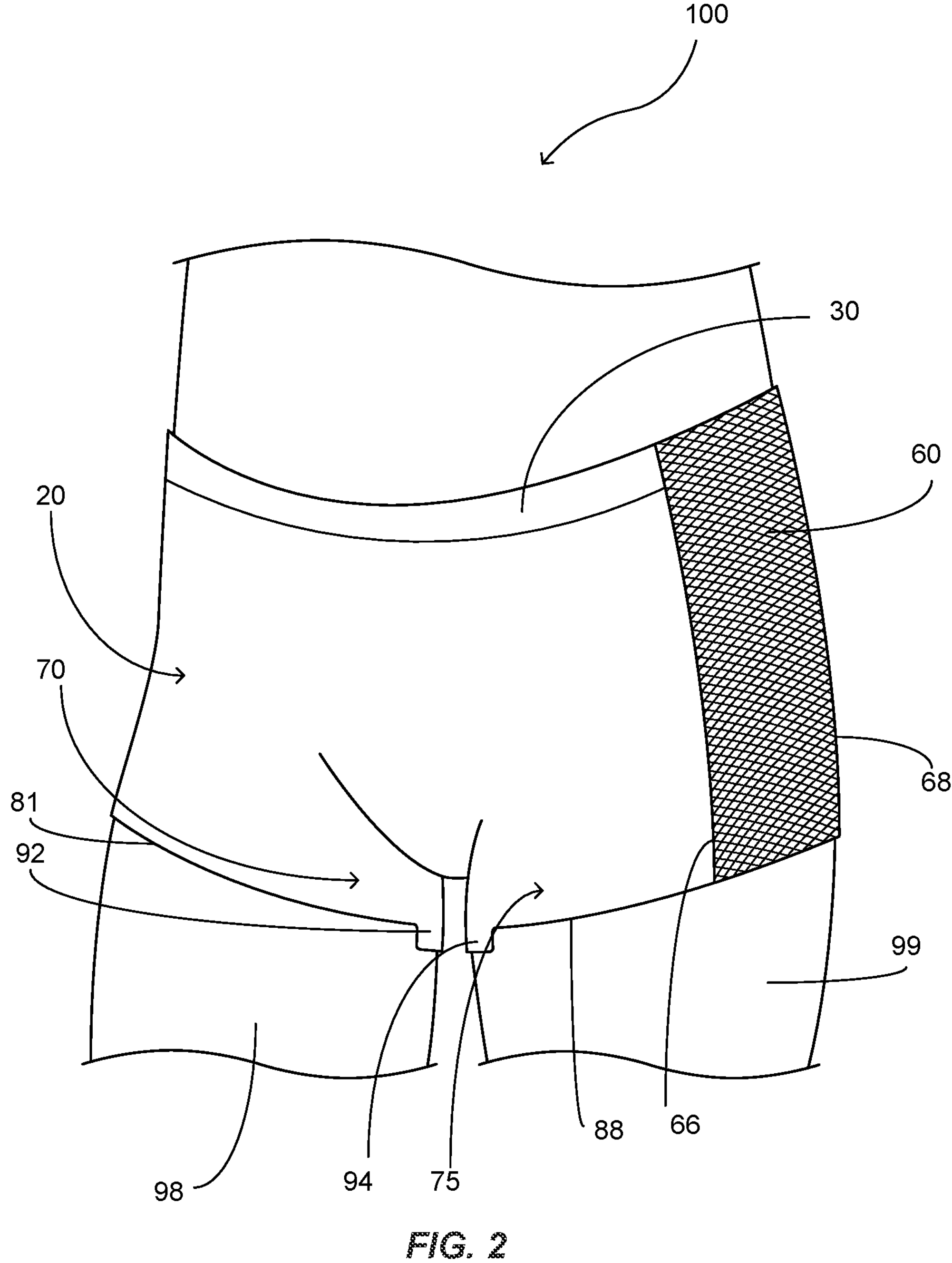
FIG. 2 is a front perspective view of the preferred embodiment of the present invention.

Referring now to the drawings submitted herewith, wherein various elements depicted therein are not necessarily drawn to scale and wherein through the views and figures like elements are referenced with identical reference numerals, there is illustrated a feminine hygiene product 100 constructed according to the principles of the present invention.

An embodiment of the present invention is discussed herein with reference to the figures submitted herewith. Those skilled in the art will understand that the detailed description herein with respect to these figures is for explanatory purposes and that it is contemplated within the scope of the present invention that alternative embodiments are plausible. By way of example but not by way of limitation, those having skill in the art in light of the present teachings of the present invention will recognize a plurality of alternate and suitable approaches dependent upon the needs of the particular application to implement the functionality of any given detail described herein, beyond that of the particular implementation choices in the embodiment described herein. Various modifications and embodiments are within the scope of the present invention.

It is to be further understood that the present invention is not limited to the particular methodology, materials, uses and applications described herein, as these may vary. Furthermore, it is also to be understood that the terminology used herein is used for the purpose of describing particular embodiments only, and is not intended to limit the scope of the present invention. It must be noted that as used herein and in the claims, the singular forms “a”, “an” and “the” include the plural reference unless the context clearly dictates otherwise. Thus, for example, a reference to “an element” is a reference to one or more elements and includes equivalents thereof known to those skilled in the art. All conjunctions used are to be understood in the most inclusive sense possible. Thus, the word “or” should be understood as having the definition of a logical “or” rather than that of a logical “exclusive or” unless the context clearly necessitates otherwise. Structures described herein are to be understood also to refer to functional equivalents of such structures. Language that may be construed to express approximation should be so understood unless the context clearly dictates otherwise.

References to “one embodiment”, “an embodiment”, “exemplary embodiments”, and the like may indicate that the embodiment(s) of the invention so described may include a particular feature, structure or characteristic, but not every embodiment necessarily includes the particular feature, structure or characteristic.

Referring in particular to the Figures submitted herewith, the feminine hygiene product 100 includes a body 10. It should be understood within the scope of the present invention that the body 10 could be provided in alternate sizes and colors. The body 10 in a preferred embodiment of the present invention is manufactured to have a boxer short style. This shape of the body 10 provides substantial coverage of the pelvic area of a wearer, in particular the upper leg area, inner upper thigh and buttocks in addition to traditional groin areas. The coverage provided by the construction of the body 10 provides additional area and material of the body 10 that is configured to provide absorption of bodily fluids.

The body 10 includes a front wall 20 wherein the front wall panel 20 is manufactured from a first layer 22 and a second layer 24. The first layer 22 and second layer 24 are operably coupled utilizing suitable durable techniques such as but not limited to stitching. The first layer 22 is the outermost layer and is manufactured from a material such as but not limited to spandex. The second layer 24 is adjacent a wearer’s skin subsequent donning of the feminine hygiene product 100. The second layer 24 is manufactured from an absorbent material such as but not limited to a superabsorbent polymer. The front wall panel 20 includes a waistband 30 proximate the top thereof. The waistband 30 extends across the full width of the front wall panel 20 and is manufactured from a stretchable material such as but not limited to elastane. The waistband 30 provides an ability for the upper portion of the front wall panel 20 to be stretched during the donning process and further provides a secure fit ensuing the feminine hygiene product 100 being donned by a wearer.

The body 10 further includes a rear wall panel 40. The rear wall panel 40 is manufactured from a first layer 42 and a second layer 44. The first layer 42 and second layer 44 are operably coupled utilizing suitable durable techniques such as but not limited to stitching. The first layer 42 is the outermost layer and is manufactured from a material such as but not limited to spandex. The second layer 44 is adjacent a wearer’s skin subsequent donning of the feminine hygiene product 100. The second layer 44 is manufactured from an absorbent material such as but not limited to a superabsorbent polymer. While not particularly illustrated herein, it should be understood within the scope of the present invention that the waistband 30 extends circumferentially around the body 10 and as such is proximate the upper perimeter of the rear wall panel 40.

Intermediate the front wall panel 20 and rear wall panel 40 are side panels 60,65. Side panels 60, 65 include longitudinal edges 66,68 that are operably coupled to the front wall panel 20 and rear wall panel 40 respectively utilizing suitable techniques such as but not limited to stitching. The side panels 60,65 are manufactured from a single layer of material such as but not limited to elastane. The side panels 60,65 provide a stretch to the body 10 that is utilized during donning and further provides a slight compression force so as to maintain the body 10 against the wearer with a biased force enabling capture of all bodily fluids preventing leakage thereof.

The body 10 includes upper leg portions 70, 75 that are circumferentially disposed around the legs 98,99 of the wearer and integrally formed with the front wall panel 20 and rear wall panel 40. The upper leg portions 70,75 include lower perimeter edges 87,88. Integrally formed into the lower perimeter edges 87, 88 are tab members 92,94. Tab members 92,94 are rectangular in shape extending downward from the lower perimeter edges 87,88 being proximate the upper inner thigh of the wearer. The tab members 92, 94 extend along the inner upper thigh from the front wall panel 20 terminating at a lower edge of the rear wall panel 40. The tab members 92, 94 are manufactured of two layers as the front wall panel 20 and rear wall panel 40 with the layer adjacent the wearer being comprised of an absorbent material. The tab members 92,94 provide a structure that ensures capture of any bodily fluids present in the groin area so as to inhibit the fluids from egressing past the tab members 92,94.

In the preceding detailed description, reference has been made to the accompanying drawings that form a part hereof, and in which are shown by way of illustration specific embodiments in which the invention may be practiced. These embodiments, and certain variants thereof, have been described in sufficient detail to enable those skilled in the art to practice the invention. It is to be understood that other suitable embodiments may be utilized and that logical changes may be made without departing from the spirit or scope of the invention. The description may omit certain information known to those skilled in the art. The preceding detailed description is, therefore, not intended to be limited to the specific forms set forth herein, but on the contrary, it is intended to cover such alternatives, modifications, and equivalents, as can be reasonably included within the spirit and scope of the appended claims.

What is claimed is:

1. A feminine hygiene product configured to capture and retain bodily fluids wherein the feminine hygiene product comprises:

a body, said body having a first layer and a second layer, said first layer and said second layer being adjacent and operably coupled, said body having a front wall panel and a rear wall panel, said front wall panel and said rear wall panel having opposing side panels operably coupled intermediate the front wall panel and rear wall panel, said second layer of said body configured to be positioned adjacent a user, said second layer being manufactured from an absorbent material, said body further having upper leg portions, said upper leg portions being integrally formed with said front wall panel and said rear wall panel, said upper leg portions having a lower perimeter edge, said first layer of said body being manufactured from elastane, said opposing side panels being comprised of a single layer; and tab members, said tab members being integrally formed with said lower perimeter edge of said upper leg portions, said tab members extending downward from said lower perimeter edge and extending from said front wall panel to said rear wall panel, said tab members being configured to be positioned adjacent a groin area of the wearer; and wherein said body is configured to provide coverage of a pelvic area of a wearer.

2. The feminine hygiene product configured to capture and retain bodily fluids as recited in claim 1, wherein said opposing side panels are manufactured from elastane.

3. The feminine hygiene product configured to capture and retain bodily fluids as recited in claim 2, wherein said body further including a waistband, said waistband extending around a top of said body.

4. The feminine hygiene product configured to capture and retain bodily fluids as recited in claim 3, wherein said body is formed in a boxer short style.

* * * * *